(12) United States Patent
Miller et al.

(10) Patent No.: US 12,357,327 B2
(45) Date of Patent: Jul. 15, 2025

(54) SURGICAL GUIDE INSTRUMENT DEVICES AND METHODS

(71) Applicant: Mayo Foundation for Medical Education and Research, Rochester, MN (US)

(72) Inventors: Kai J. Miller, Rochester, MN (US); Thomas J. Richner, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 358 days.

(21) Appl. No.: 18/101,787

(22) Filed: Jan. 26, 2023

(65) Prior Publication Data

US 2023/0233217 A1 Jul. 27, 2023

Related U.S. Application Data

(60) Provisional application No. 63/303,271, filed on Jan. 26, 2022.

(51) Int. Cl.
*A61B 17/17* (2006.01)
*A61N 1/05* (2006.01)

(52) U.S. Cl.
CPC ........ *A61B 17/1739* (2013.01); *A61N 1/0539* (2013.01)

(58) Field of Classification Search
CPC . A61B 17/1739; A61B 17/686; A61B 17/688; A61B 17/1695; A61B 90/14; A61N 1/0536

USPC .......................................... 606/96, 172, 167
See application file for complete search history.

(56) References Cited

U.S. PATENT DOCUMENTS

| | | | |
|---|---|---|---|
| 906,085 A * | 12/1908 | Tolman | A61B 17/32 132/73 |
| 5,122,144 A * | 6/1992 | Bert | A61B 17/1764 606/88 |
| 5,769,856 A * | 6/1998 | Dong | A61B 17/1778 606/80 |
| 6,022,356 A * | 2/2000 | Noyes | A61B 17/1764 606/88 |
| D436,689 S * | 1/2001 | Ortiz | D28/9 |
| 6,364,910 B1 * | 4/2002 | Shultz | A61B 17/1684 606/86 R |
| 6,673,115 B2 * | 1/2004 | Resch | A61B 17/1684 606/86 R |
| 7,473,259 B2 * | 1/2009 | Jacobs | A61B 17/0482 606/148 |
| 7,580,756 B2 * | 8/2009 | Schulte | A61N 1/0539 607/116 |
| 7,949,410 B2 * | 5/2011 | Rodriguez | A61N 1/0531 607/116 |

(Continued)

OTHER PUBLICATIONS

[No Author Listed], "Guardian Cranial Burr Hole Cover System Clinician's Manual," St. Jude Medical, Aug. 2016, 28 pages.

(Continued)

*Primary Examiner* — Jessica Weiss
(74) *Attorney, Agent, or Firm* — Fish & Richardson P.C.

(57) ABSTRACT

Systems, devices and methods are described for surgical guide instruments. For example, this disclosure describes surgical guide instruments for assisting in countersinking shelves for deep brain stimulation lead locking mechanisms.

8 Claims, 5 Drawing Sheets

(56) References Cited

U.S. PATENT DOCUMENTS

| | | | | |
|---|---|---|---|---|
| 8,417,353 | B2* | 4/2013 | Appenrodt | A61N 1/0539 |
| | | | | 607/139 |
| 8,708,699 | B2* | 4/2014 | Suter | A61C 1/084 |
| | | | | 433/75 |
| 11,109,937 | B2* | 9/2021 | Zadeh | A61B 17/0482 |
| 2005/0015153 | A1* | 1/2005 | Goble | A61F 2/3859 |
| | | | | 606/88 |
| 2005/0192594 | A1* | 9/2005 | Skakoon | A61B 90/50 |
| | | | | 606/129 |
| 2008/0255582 | A1* | 10/2008 | Harris | A61B 5/293 |
| | | | | 606/129 |
| 2012/0197261 | A1* | 8/2012 | Rocci | A61B 17/1686 |
| | | | | 606/96 |
| 2013/0103152 | A1* | 4/2013 | Kwon | A61B 17/7064 |
| | | | | 623/17.16 |
| 2014/0324060 | A1* | 10/2014 | Siebold | A61B 17/1764 |
| | | | | 700/98 |

OTHER PUBLICATIONS

[No Author Listed], "SenSight Burr Hole Device Manual," Medtronic, Jul. 2021, 16 pages.

[No Author Listed], "SureTek Burr Hole Cover Directions for Use," Boston Scientific, Nov. 2017, 12 pages.

Barrett et al., "Technical Note: Preemptive Surgical Revision of Impending Deep Brain Stimulation Hardware Erosion," World Neurosurg., Mar. 2018, 111:41-46.

Giller et al., "Some technical nuances for deep brain stimulator implantation," Inrerdisciplinary Neurosurgery, Mar. 2015, 2(1):29-39.

Miller et al., "A Stencil Instrument for Countersinking Deep Brain Stimulator Lead Anchoring Devices," World Neurosurg., Nov. 2022, 167:98-101.

Morishita et al., "Postoperative lead migration in deep brain stimulation surgery: Incidence, risk factors, and clinical impact," PLoS One, Sep. 2017, 12(9):e0183711.

Park et al., "A Combination Procedure with Double C-Shaped Skin Incision and Dual-Floor Burr Hole Method to Prevent Skin Erosion on the Scalp and Reduce Postoperative Skin Complications in Deep Brain Stimulation," Stereotact. Funct. Neurosurg., Apr. 2011, 89(3):178-184.

Shin et al., "DBS Revision Surgery: Indications and Nuances," In: Surgery for Parkinson's Disease, Goodman (ed)., Springer, Dec. 2018, Chapter 8, pp. 91-104.

Sixel-Döring et al., "Skin complications in deep brain stimulation for Parkinson's disease: frequency, time course, and risk factors," Acta Neurochir., Feb. 2010, 152(2):195-200.

Yamamoto et al., "Dual-floor burr hole adjusted to burr hole ring and cap for implantation of stimulation electrodes," J. Neurosurg., Oct. 2003, 99(4):783-784.

Zhou et al., "Long-Term Effect of Modified Incision to Prevent Related Complications in Deep Brain Stimulation," World Neurosurg., Sep. 2018, 117:280-283.

\* cited by examiner

SURGICAL GUIDE INSTRUMENT DEVICES AND METHODS

CROSS-REFERENCE TO RELATED APPLICATIONS

This application claims the benefit of U.S. Patent Application Ser. No. 63/303,271, filed on Jan. 26, 2022. The disclosure of the prior application is considered part of (and is incorporated by reference in) the disclosure of this application.

BACKGROUND

1. Technical Field

This disclosure relates to systems, devices and methods for surgical guide instruments. For example, this disclosure relates to surgical guide instruments for assisting in countersinking shelves for deep brain stimulation lead locking mechanisms.

2. Background Information

Deep brain stimulation (DBS) surgery involves making a burr hole in a skull of a patient through which a multi-contact electrode lead is advanced into the brain beneath. To hold a DBS lead in a fixed position above the target area, a skull-mounted device can be placed over the burr hole. The skull-mounted devices can include a base ring, a locking clip, and a cap.

The use of these locking devices can be a tool in standardization of surgical workflow, and they guard against lead migration. The locking devices also prevent rotation of directional leads after locking. The use of locking devices has been adopted by the functional neurosurgery community and is the FDA "on-label" technique for lead fixation promoted by DBS manufacturers.

A side effect of these lead-locking mechanisms is that they produce a "proud" profile on the scalp. In response, surgeons may countersink the DBS anchoring devices by drilling out a shelf around the burr hole through the outer table of the skull and part (or all) of the cancellous bone beneath, preserving the inner table of the skull.

There are at least two advantages of countersinking DBS lead-locking mechanisms. The first is that there is risk of erosion and infection because of the proud nature of the anchoring device. Countersinking reduces this risk significantly. The second advantage of countersinking is improved cosmesis. The anchoring devices can produce much-maligned "horns" from scalp bulging, particularly in bald patients. By bringing this profile down, the bulging is reduced or prevented, depending on the thickness of the skull (which can limit the depth of countersink possible).

However, countersinking comes at the price of added surgical time. Additionally, there is a potential for divots and troughs in the scalp if the countersinking contour is not tightly matched to the profile of the base ring.

SUMMARY

This disclosure describes systems, devices and methods for surgical guide instruments. For example, this disclosure describes surgical guide instruments for assisting in countersinking shelves for deep brain stimulation lead locking mechanisms.

One general aspect includes a surgical guide instrument. The surgical guide instrument also includes a first end having a circular ring that extends around a center aperture and one or more protrusions extending from an outer surface the circular ring. The instrument also includes a second end having an ovular ring that extends around an ovular aperture, the ovular ring having a bar that extends across the ovular aperture, the bar having a disc centered in the ovular aperture. The instrument also includes an arm that extends between the first end and the second end. Other embodiments of this aspect include corresponding computer systems, apparatus, and computer programs recorded on one or more computer storage devices, each configured to perform the actions of the methods.

Implementations may include one or more of the following features. The surgical guide instrument where the arm has one or more angled portions that set a height difference between the first end and the second end. The one or more protrusions may include three protrusions positioned at 90-degree intervals from each other. The disc is configured to fit in a burr hole in a skull of a patient. The burr hole is drilled through the first end. The ovular ring defines a drill area within the ovular aperture around the disc for drilling a countersunk shelf.

One general aspect includes a method of countersinking deep brain stimulator lead anchoring devices. The method of countersinking deep brain stimulator also includes providing a surgical guide instrument, the surgical guide instrument may include: a first end having a circular ring that extends around a center aperture and one or more protrusions extending from an outer surface the circular ring; a second end having an ovular ring that extends around an ovular aperture, the ovular ring having a bar that extends across the ovular aperture, the bar having a disc centered in the ovular aperture; an arm that extends between the first end and the second end. The stimulator also includes aligning the one or more protrusions with centering marks in a treatment area. The stimulator also includes drilling a burr hole through the circular ring. The stimulator also includes seating the disc in the burr hole. The stimulator also includes drilling a countersunk shelf through the ovular aperture.

Implementations may include one or more of the following features. The method may include: seating a base ring of a deep brain stimulator lead on the countersunk shelf; and securing the base ring to the countersunk shelf.

Particular embodiments of the subject matter described in this document can be implemented to realize one or more of the following advantages. The guide instrument is hand-held, has a low profile, and does not introduce additional steps to the surgical procedure, which makes it easy to use. The guide instrument facilitates an increased speed of the surgery by assisting an experienced neurosurgeon to take approximately 3-5 minutes for generating the burr hole and countersinking profile. The guide instrument shape ensures a tight fit to the lead anchoring device, so that the countersunk shelf will not have grooves and/or defects in circumference around locking ring after it has been screwed in place. The guide instrument is easy to clean, and it is not easily deformed.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This disclosure describes systems, devices and methods for surgical guide instruments. For example, this disclosure describes surgical guide instruments for assisting in countersinking shelves for deep brain stimulation lead locking mechanisms.

Figure 1:
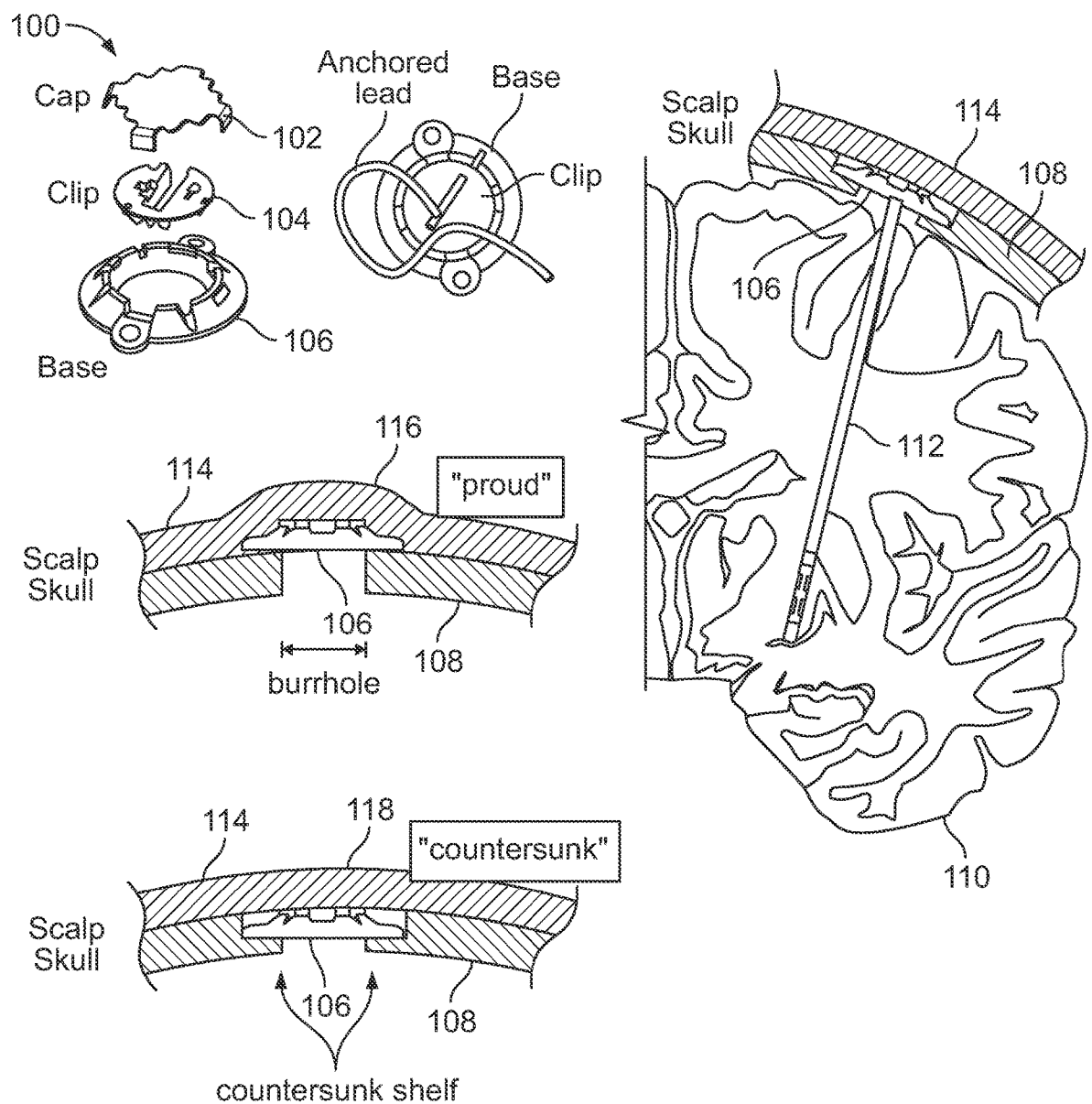
FIG. 1 is a schematic diagram of deep brain stimulation components and implant options.

Referring to FIG. 1, a schematic diagram of deep brain stimulation components and implant options is shown. A lead-locking mechanism 100 includes a cap 102, a locking clip 104, and a base ring 106. The base ring 106 is screwed into the outer convexity of the skull 108, with an opening centered around the burr hole. After the DBS lead 112 has been advanced into the brain 110, but while it is still held above, the locking clip 104 is placed into the base ring 106 around the DBS lead 112, and then slid closed. The locking clip 104 anchors the DBS lead 112 into place within the base ring 106. The cap 102 is slid down over the anchored construct prior to closure of the scalp 114 above the cap 102.

In an implantation, the base ring 106 is situated above the burr hole, which raises the scalp 114 above the base ring 106 and creates a "proud" profile 116. In some implantations, a surgeon can countersink the base ring 106 to leave a flush profile 118 of the scalp 114 for decreased risk of erosion and improved cosmesis.

Figure 2:
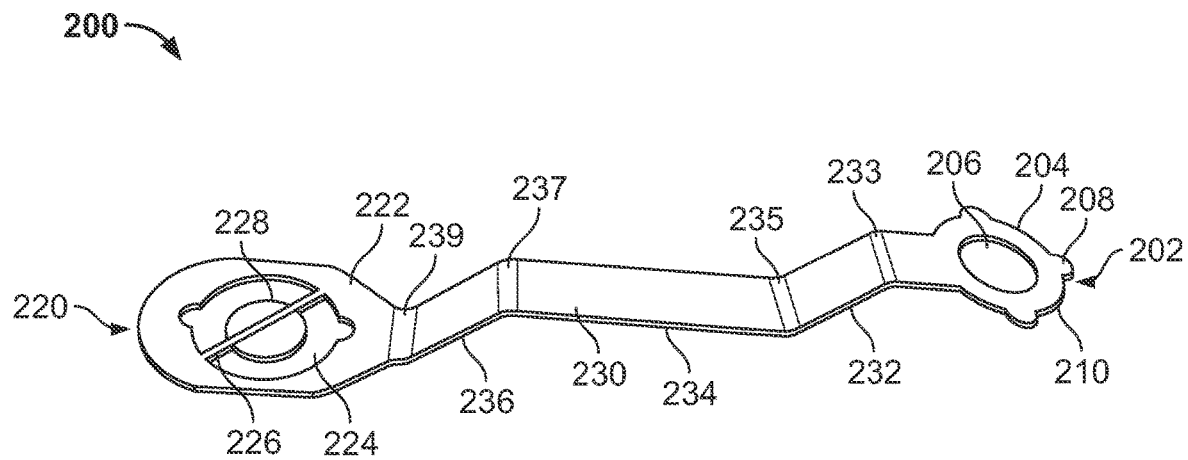
FIG. 2 is a perspective side view of an example surgical guide instrument in accordance with some embodiments.
Figure 3:
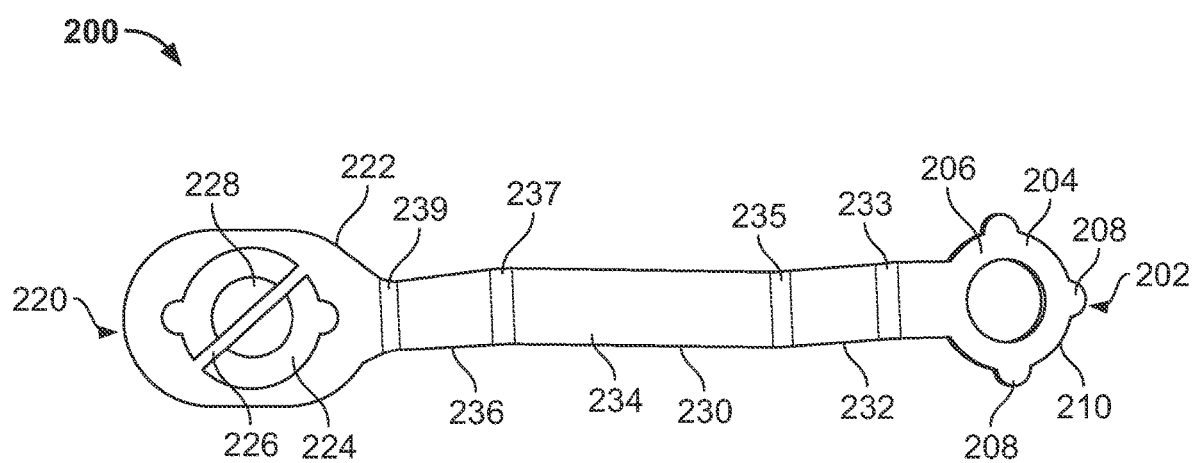
FIG. 3 is a top view of the surgical guide instrument of FIG. 2.

Referring to FIGS. 2 and 3, a surgical guide instrument 200 is shown. The surgical guide instrument 200 is used for assisting in countersinking shelves in the skull of a patient for deep brain stimulation lead locking mechanisms. The surgical guide instrument 200 includes a first end 202, a second end 220, and an arm 230 that extends between the first end 202 and the second end 220.

Figure 4:
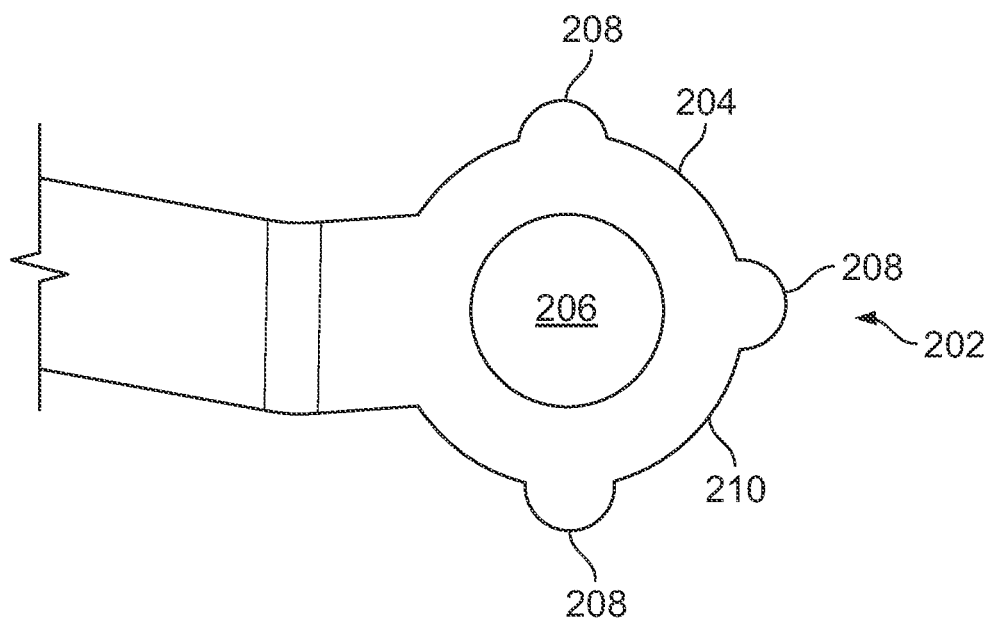
FIG. 4 shows a top view of a first end of the surgical guide instrument of FIG. 2.

Referring to FIGS. 2-4, the first end 202 has a circular ring 204 that extends around a center aperture 206. The circular ring 204 has one or more protrusions 208 extending from an outer surface 210 the circular ring 204. For example, the first end 202 can include three protrusions 208 positioned at 90-degree intervals from each other. The first end 202 is configured so that a burr hole in the skull of a patient can be drilled through the center aperture 206 in the circular ring 204. The one or more protrusions 208 can be aligned with cross hairs drawn in the target area to center the first end 202 over the desired burr hole location.

Figure 5:
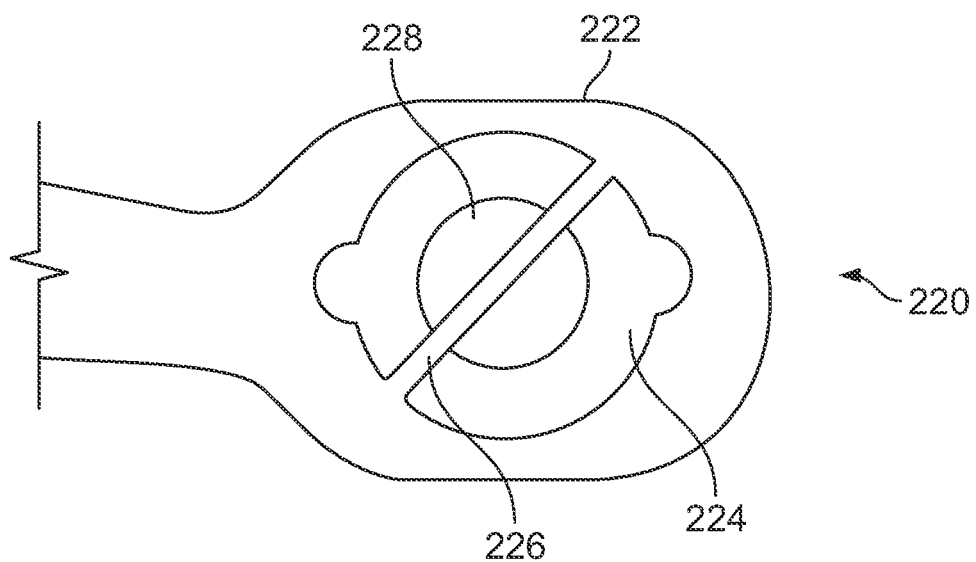
FIG. 5 shows a top view of a second end of the surgical guide instrument of FIG. 2.

Referring to FIGS. 2, 3, and 5, the second end 220 can be positioned at an opposite end of the surgical guide instrument 200 from the first end 202. The second end 220 has an ovular ring 222 that extends around an ovular aperture 224. The ovular ring 224 has a bar 226 that extends across the ovular aperture 224. In some aspects, the bar 226 can extend across the ovular aperture at or near a 45 degree angle. The bar 226 has a disc 228 that is centered in the ovular aperture 224. The disc 228 is configured to fit in the burr hole in the skull of a patient that is drilled through the first end 202.

With the disc 228 seated in the burr hole, the ovular ring 222 defines a drill area within the ovular aperture 224 around the disc 228 for drilling a countersunk shelf in the skull of the patient. The countersunk shelf is drilled through the ovular aperture 224 in the ovular ring 222.

Referring again to FIGS. 2 and 3, the arm 230 connects the first end 202 and the second end 220 to each other. The arm 230 includes a first angled portion 232, a center portion 234, and a second angled portion 236. The first angled portion 232 is connected to the first end 202. The first angled portion 232 is connected to the first end 202 at a first bend 233 that facilitates the extension of the first angled portion 232 away from the first end 202 at an angle. In some aspects, the angle can be between 0 and 90 degrees, between 10 and 80 degrees, between 20 and 70 degrees, between 30 and 60 degrees, between 40 and 50 degrees, and at or near 45 degrees.

The center portion 234 is positioned between the first angled portion 232 and the second angled portion 236. The center portion 234 is connected to the first angled portion at a second bend 235. The second bend 235 facilitates a transition in the arm 230 from the first angled portion 232 to the center portion 234, the center portion 234 is oriented at the same or a similar angle to the first end 202 and the second end 220. For example, if the first end 202 and the second end 220 were arranged to be level (e.g., using a spirit level at each of the first end 202 and second end 220) the center portion 234 could also be at or near level. Each of the first end 202, the second end 220, and the center portion 234 can be arranged at the same angle, and can each be at a different height.

The center portion 234 is connected to the second angled portion 236 at a third bend 237. The third bend 237 facilitates the extension of the second angled portion 236 between the center portion 234 and the second end 220 at an angle. In some aspects, the angle can be between 0 and 90 degrees, between 10 and 80 degrees, between 20 and 70 degrees, between 30 and 60 degrees, between 40 and 50 degrees, and at or near 45 degrees.

The second angled portion 236 is connected to the second end 220. The second angled portion 236 can be connected to the second end 220 at a fourth bend 239 that facilitates the extension of the second angled portion 236 away from the second end 220 at an angle. In some aspects, the angle can be the same as the angle at the third bend 237. For example, the angle can be between 0 and 90 degrees, between 10 and 80 degrees, between 20 and 70 degrees, between 30 and 60 degrees, between 40 and 50 degrees, and at or near 45 degrees.

The first angled portion 232, the center portion 234, and the second angled portion 236 provide a height difference between the first end 202 and the second end 220. The height difference between the first end 202 and the second end 220 allow each end to come down flush to the surface of the skull In some aspects, the surgical guide instrument 100 can be manufactured using metal materials (e.g., medical grade metals). The surgical guide instrument 100 can also be manufactured using other materials such as medical grade plastics, disposable materials, or other suitable materials.

Referring to FIGS. 6A-6G, the steps of a method of countersinking deep brain stimulator lead anchoring devices are illustrated. The method utilizes a surgical guide instrument such as surgical guide instrument 200 to drill a full thickness burr hole 310 in the skull of a patient and to drill a countersunk shelf 312 around the burr hole.

Figure 6A:
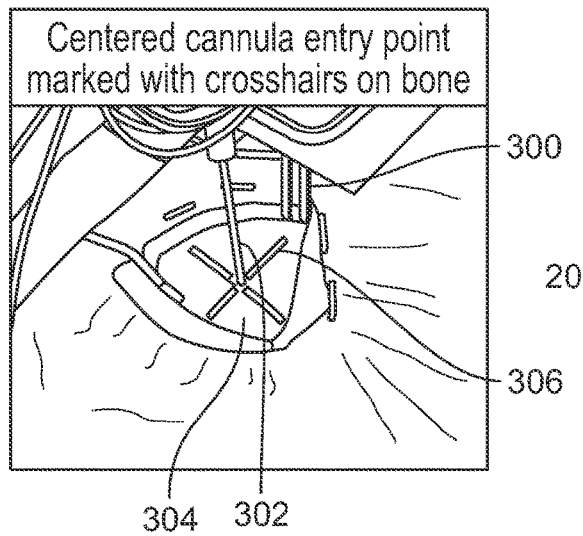
FIG. 6A shows a step of an example surgical procedure using the surgical guide instrument of FIG. 2 in accordance with some embodiments.

As shown in FIG. 6A, a targeting mechanism 300 is used to stereotactically align a trajectory to target (e.g., using a Leksell frame). The cannula 302 is lowered along the trajectory to the bone 304, and crosshairs 306 are drawn to facilitate centering. These crosshairs 306 are drawn to a wide diameter so that centering can be continuously validated. When this step is not performed, the burr hole can drift while drilling.

Figure 6B:
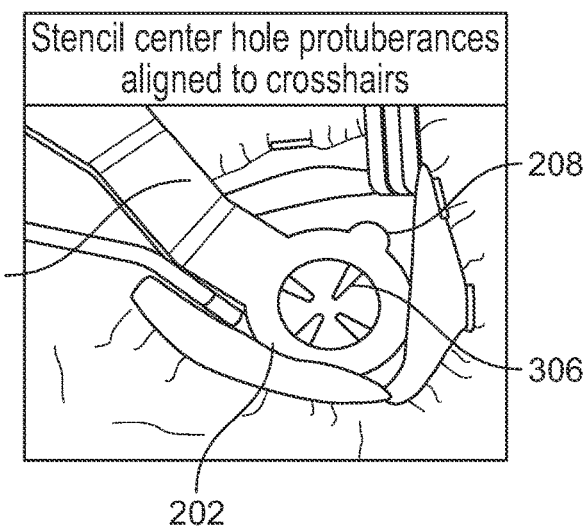
FIG. 6B shows another step of the surgical procedure using the surgical guide instrument of FIG. 2.

As shown in FIG. 6B, the method includes providing a surgical guide instrument, such as surgical guide instrument 200 described above. The first end 202 of the surgical guide instrument 200 is aligned to the crosshairs 306 using the one or more protrusions 208 extending from the outer surface 210 the circular ring 204.

Figure 6C:
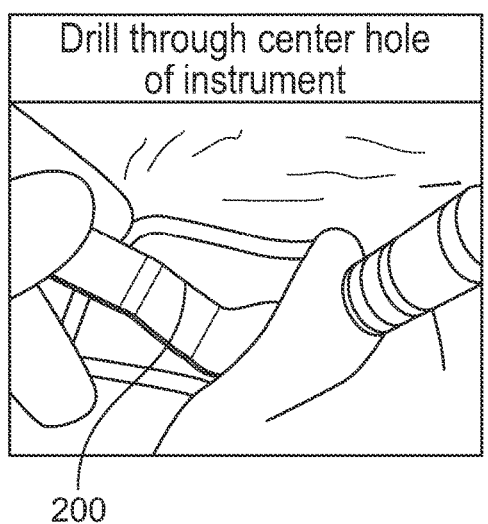
FIG. 6C shows another step of the surgical procedure using the surgical guide instrument of FIG. 2.
Figure 6D:
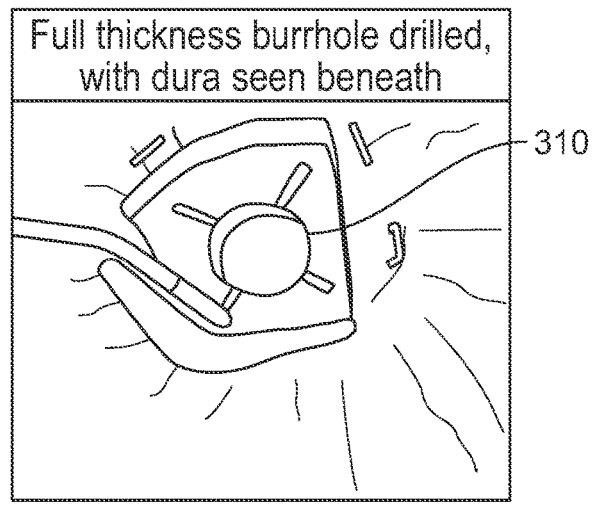
FIG. 6D shows another step of the surgical procedure using the surgical guide instrument of FIG. 2.

As shown in FIG. 6C and FIG. 6D, a surgeon then drills a full-thickness burr hole 310 through the center aperture 206 of the first end 202 of the surgical guide instrument 200. The result of the burr hole drilling in FIG. 6C is shown in FIG. 6D.

Figure 6E:
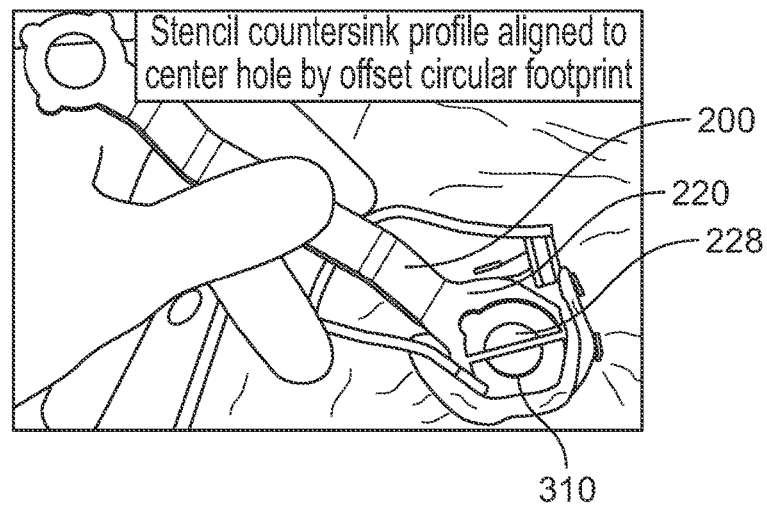
FIG. 6E shows another step of the surgical procedure using the surgical guide instrument of FIG. 2.

As shown in FIG. 6E, the disc 228 of the second end 220 of the surgical guide instrument 200 is seated in the burr hole 310. The shape of the countersinking shelf 312 is drilled directly through the ovular aperture 224 in the ovular ring 222.

Figure 6F:
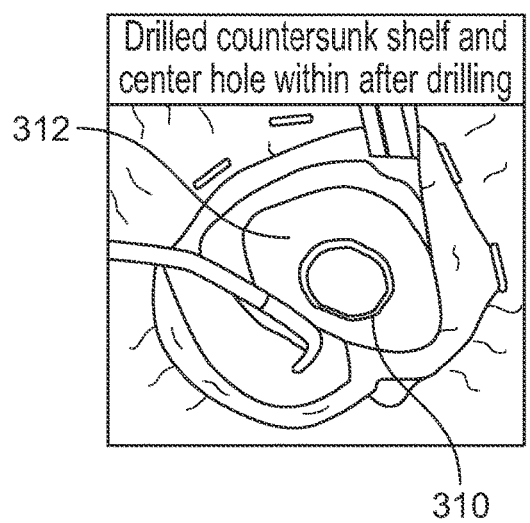
FIG. 6F shows another step of the surgical procedure using the surgical guide instrument of FIG. 2.
Figure 6G:
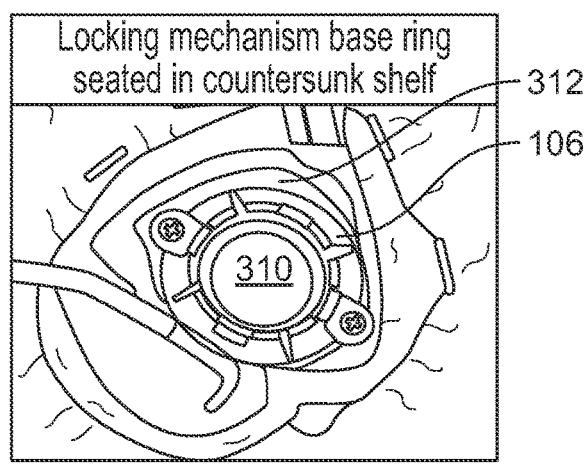
FIG. 6G shows another step of the surgical procedure using the surgical guide instrument of FIG. 2.

As shown in FIG. 6F, the drilled countersunk shelf 312 is made to an even depth using the hand drill.

As shown in FIG. 6F, the base ring 106 is seated on the countersunk shelf 312 and screwed in.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical guide instrument, the surgical guide instrument comprising:
    a first end having a circular ring that extends around a center aperture and one or more protrusions extending from an outer surface of the circular ring;
    a second end having an ovular ring that extends around an ovular aperture, the ovular ring having a bar that extends across the ovular aperture, the bar having a disc centered in the ovular aperture; and
    an arm that extends between the first end and the second end.

2. The surgical guide instrument of claim 1, wherein the arm has one or more angled portions that set a height difference between the first end and the second end.

3. The surgical guide instrument of claim 1, wherein the one or more protrusions comprises three protrusions positioned at 90-degree intervals from each other.

4. The surgical guide instrument of claim 1, wherein the disc is configured to fit in a burr hole in a skull of a patient.

5. The surgical guide instrument of claim 4, wherein the burr hole is drilled through the first end.

6. The surgical guide instrument of claim 1, wherein the ovular ring defines a drill area within the ovular aperture around the disc for drilling a countersunk shelf.

7. A method of countersinking deep brain stimulator lead anchoring devices, the method comprising:
    providing a surgical guide instrument, the surgical guide instrument comprising:
        a first end having a circular ring that extends around a center aperture and one or more protrusions extending from an outer surface of the circular ring;
        a second end having an ovular ring that extends around an ovular aperture, the ovular ring having a bar that extends across the ovular aperture, the bar having a disc centered in the ovular aperture; and
        an arm that extends between the first end and the second end;
    aligning the one or more protrusions with centering marks in a treatment area;

drilling a burr hole through the circular ring;
seating the disc in the burr hole; and
drilling a countersunk shelf through the ovular aperture.

8. The method of claim 7, further comprising:
seating a base ring of a deep brain stimulator lead on the countersunk shelf; and
securing the base ring to the countersunk shelf.

\* \* \* \* \*